US006312402B1

United States Patent
Hansmann

(10) Patent No.: US 6,312,402 B1
(45) Date of Patent: *Nov. 6, 2001

(54) ULTRASOUND CATHETER FOR IMPROVING BLOOD FLOW TO THE HEART

(75) Inventor: Douglas R. Hansmann, Bainbridge Island, WA (US)

(73) Assignee: Ekos Corporation, Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/160,221

(22) Filed: Sep. 24, 1998

(51) Int. Cl.$^7$ ................................... A61B 17/20

(52) U.S. Cl. ............................. 604/22; 600/437

(58) Field of Search .................... 601/2, 3; 604/22; 600/437, 439, 459, 461, 462, 464, 466, 467, 471

(56) References Cited

U.S. PATENT DOCUMENTS

| | | | |
|---|---|---|---|
| 3,433,226 | 3/1969 | Boyd | 128/305 |
| 4,040,414 | 8/1977 | Suroff | 128/24 |
| 4,319,580 | 3/1982 | Colley et al. | 128/661 |
| 4,354,502 | 10/1982 | Colley et al. | 128/663 |
| 4,531,943 | 7/1985 | Van Tassel et al. | 604/280 |
| 4,750,902 | 6/1988 | Wuchinich et al. | 604/22 |
| 4,808,153 | 2/1989 | Parisi | 604/22 |
| 4,870,953 | 10/1989 | Micheal et al. | 128/24 |
| 4,917,102 | 4/1990 | Miller et al. | 128/772 |
| 4,920,954 | 5/1990 | Alliger et al. | 128/24 |
| 4,924,863 | 5/1990 | Sterzer | 606/27 |
| 4,936,281 | 6/1990 | Stasz | 128/660.03 |
| 5,021,044 | 6/1991 | Sharawy | 604/53 |
| 5,163,421 | 11/1992 | Bernstein et al. | 128/24.1 |
| 5,197,946 | 3/1993 | Tachibana | 604/22 |
| 5,250,034 | 10/1993 | Appling et al. | 604/164 |
| 5,259,385 | * 11/1993 | Miller et al. | 128/662.04 |
| 5,267,954 | 12/1993 | Nita | 604/22 |
| 5,267,985 | 12/1993 | Shimada et al. | 604/290 |
| 5,269,291 | 12/1993 | Carter | 128/24 |

(List continued on next page.)

FOREIGN PATENT DOCUMENTS

| | | | | |
|---|---|---|---|---|
| 40 05 743 | 8/1991 | (DE) | | A61H/23/00 |
| 0 529 675 | 8/1992 | (EP) | | A61B/17/06 |
| 0 553 325 A1 | 4/1993 | (EP) | | B06B/1/06 |
| 0 629 382 | 11/1993 | (EP) | | A61B/17/36 |
| WO 89/04142 | 5/1989 | (WO) | | A61B/8/12 |
| WO 95/01751 | 1/1995 | (WO) | | A61B/8/12 |
| WO 96/29935 | 10/1996 | (WO) | | A61B/8/12 |
| WO 97/29701 | 8/1997 | (WO) | | A61B/17/22 |
| WO 98/11826 | 3/1998 | (WO) | | A61B/17/00 |
| WO 98/48711 | 11/1998 | (WO) | | A61B/17/22 |

OTHER PUBLICATIONS

Hynynen et al.; "Small Cylindrical Ultrasound Sources For Induction of Hyperthermia Via Body Cavities or Interstitial Implants"; Arizona Cancer Center and Department of Radiation Oncology, University of Arizona Health Sciences Center; vol. 9, No. 2; pp. 263–274; 1993.

Lee et al.; "Arrays of Multielement Ultrasound Applicators For Interstitial Hyperthermia"; *IEEE Transactions on Biomedical Engineering*; vol. 46, No. 7; Jul. 1999.

Primary Examiner—Sharon Kennedy
Assistant Examiner—Kevin C. Sirmons
(74) Attorney, Agent, or Firm—Wilson, Sonsini, Goodrich & Rosati

(57) ABSTRACT

A catheter useful for improving blood flow to a patient's heart has an elongated catheter body with a proximal end and a distal end. The elongated catheter body defines a catheter lumen. The elongated catheter body has an introducer distal portion with a tissue piercing distal end. An ultrasound transducer is positioned in the introducer distal portion.

5 Claims, 7 Drawing Sheets

U.S. PATENT DOCUMENTS

| | | | |
|---|---|---|---|
| 5,286,254 | 2/1994 | Shapland et al. | 604/21 |
| 5,295,484 * | 3/1994 | Marcus et al. | 128/660.03 |
| 5,304,115 | 4/1994 | Pflueger et al. | 604/22 |
| 5,318,014 | 6/1994 | Carter | 601/2 |
| 5,323,769 | 6/1994 | Bommannan et al. | 601/2 |
| 5,327,891 | 7/1994 | Rammler | 128/658 |
| 5,328,470 | 7/1994 | Nabel et al. | 604/101 |
| 5,344,435 | 9/1994 | Turner et al. | 607/101 |
| 5,345,940 * | 9/1994 | Seward et al. | 128/662.06 |
| 5,353,798 | 10/1994 | Sieben | 128/662.06 |
| 5,354,279 | 10/1994 | Hofling | 604/164 |
| 5,362,309 | 11/1994 | Carter | 604/22 |
| 5,363,853 | 11/1994 | Lieber | 128/662.06 |
| 5,380,273 | 1/1995 | Dubrul et al. | 604/22 |
| 5,385,148 * | 1/1995 | Lesh et al. | 128/662.06 |
| 5,390,678 | 2/1995 | Gesswein et al. | 128/662.06 |
| 5,421,338 | 6/1995 | Crowley et al. | 128/662.06 |
| 5,423,797 | 6/1995 | Sorin et al. | 606/1 |
| 5,431,663 | 7/1995 | Carter | 604/128 |
| 5,445,155 | 8/1995 | Sieben | 128/660.07 |
| 5,447,509 | 9/1995 | Mills et al. | 606/1 |
| 5,458,568 | 10/1995 | Racchini et al. | 604/19 |
| 5,465,726 | 11/1995 | Dickinson et al. | 128/663.01 |
| 5,474,530 | 12/1995 | Passafaro et al. | 604/22 |
| 5,474,531 | 12/1995 | Carter | 604/22 |
| 5,498,238 | 3/1996 | Shapland et al. | 604/53 |
| 5,509,896 | 4/1996 | Carter | 604/21 |
| 5,514,092 | 5/1996 | Forman et al. | 604/101 |
| 5,520,189 | 5/1996 | Malinowski et al. | 128/662.03 |
| 5,599,345 * | 2/1997 | Edwards et al. | 606/41 |
| 5,599,346 * | 2/1997 | Edwards et al. | 606/41 |
| 5,603,327 | 2/1997 | Eberle | 128/662.06 |
| 5,606,974 * | 3/1997 | Castellano et al. | 128/662.06 |
| 5,617,851 | 4/1997 | Lipkovker | 128/632 |
| 5,618,275 | 4/1997 | Bock | 604/290 |
| 5,620,479 | 4/1997 | Diederich | 607/97 |
| 5,628,730 | 5/1997 | Shapland | 604/21 |
| 5,656,028 * | 8/1997 | Swartz | 604/53 |
| 5,660,180 | 8/1997 | Malinowski et al. | 128/660.03 |
| 5,695,460 | 12/1997 | Siegal et al. | 604/21 |
| 5,725,494 * | 3/1998 | Brisken | 604/22 |
| 5,749,370 * | 5/1998 | Brooks et al. | 600/585 |
| 5,916,194 * | 6/1999 | Jacobsen et al. | 604/96 |

* cited by examiner

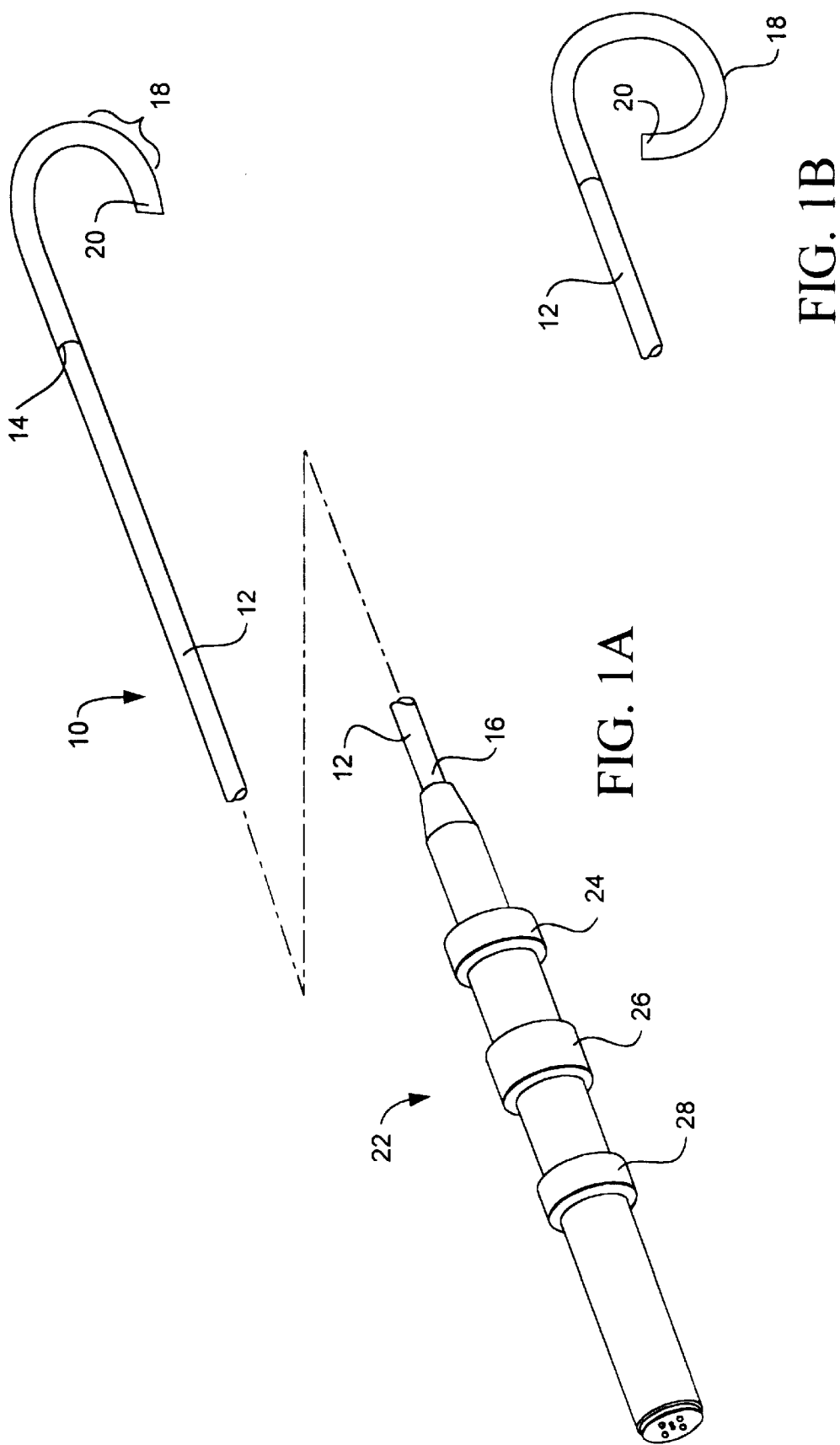

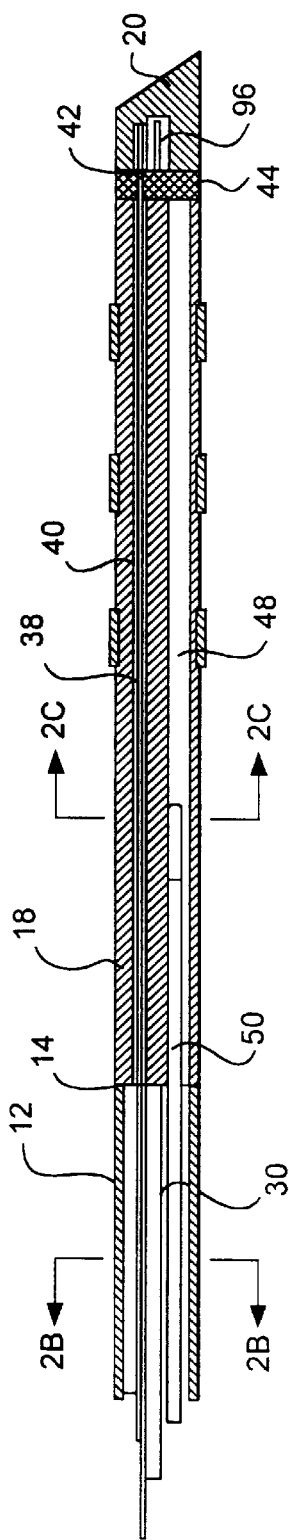
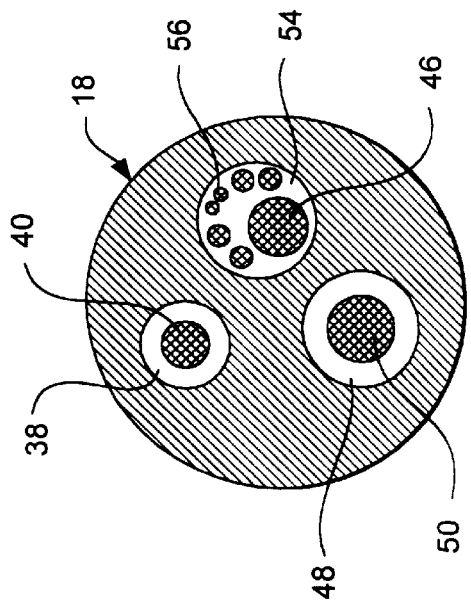
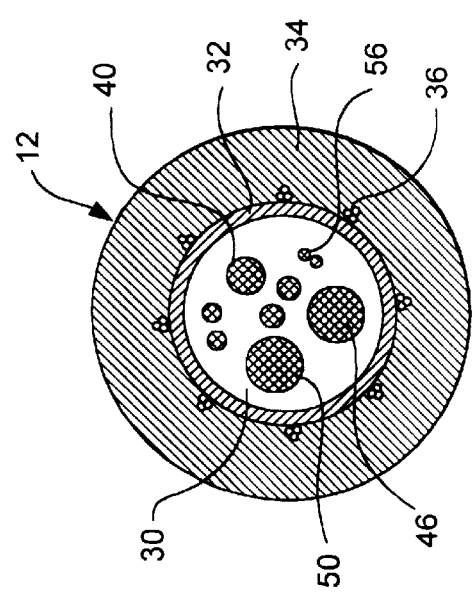
FIG. 2A
FIG. 2B
FIG. 2C

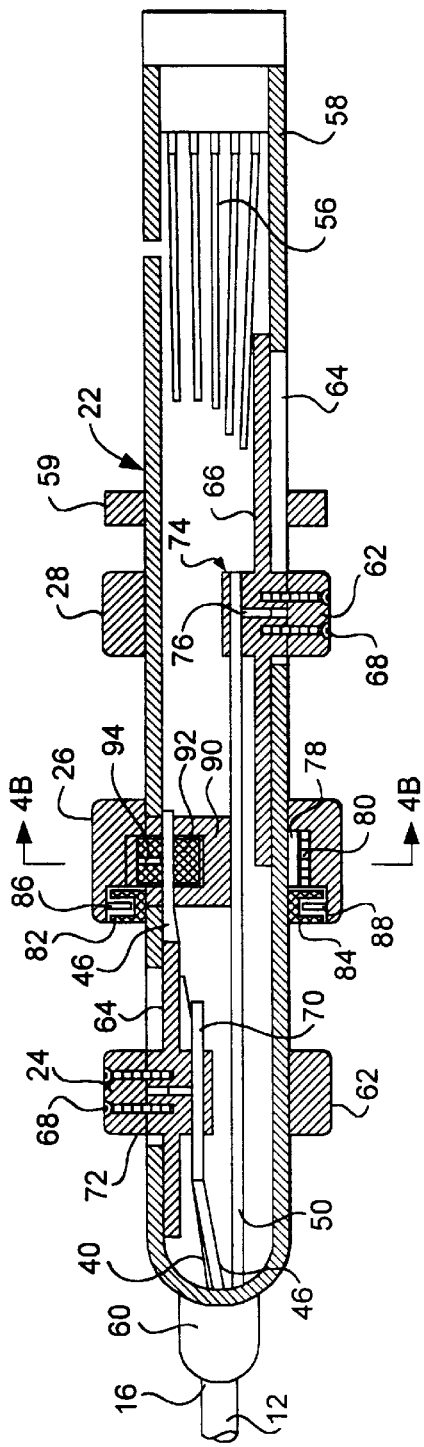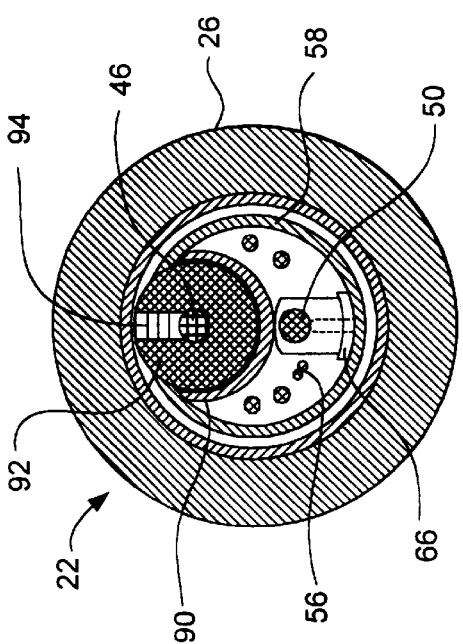
FIG. 4A
FIG. 4B

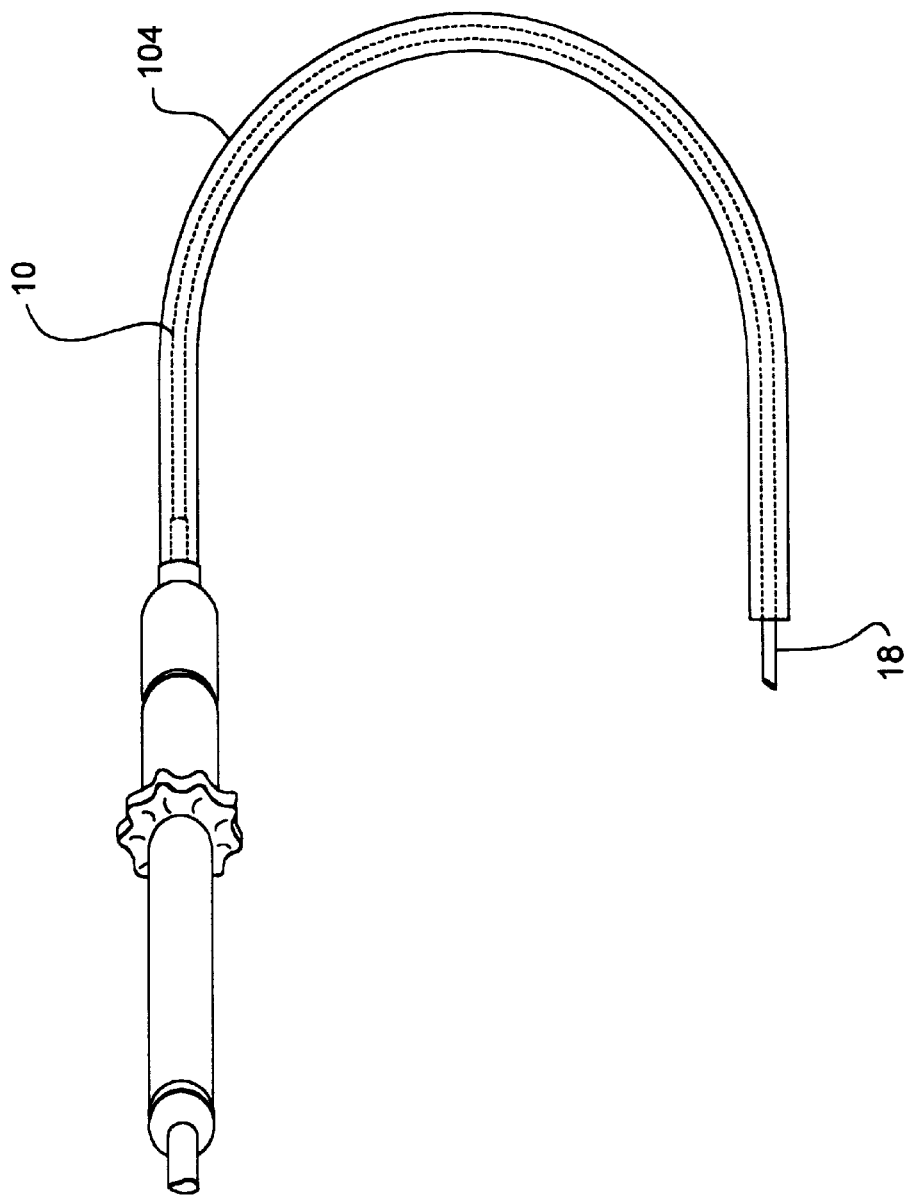

ULTRASOUND CATHETER FOR IMPROVING BLOOD FLOW TO THE HEART

BACKGROUND OF THE INVENTION

1. Field of the Invention

This invention relates to a catheter used to improve blood flow to a patient's heart, and more particularly to a catheter with an ultrasound transducer that creates revascularization channels and/or stimulates angiogenesis in a patient's heart.

2. Description of Related Art

Cardiovascular diseases are generally characterized by an impaired supply of blood to the heart or other target organs. Myocardial infarction (MI), commonly referred to as heart attacks, are a leading cause of mortality.

The number and variety of medical methods available to repair the effects of cardiovascular disease has increased rapidly over the last several years. More particularly, alternatives to open heart surgery and cardiovascular by-pass surgery have been extensively investigated, resulting in non-surgical procedures such as percutaneous transluminal coronary angioplasty, laser angioplasty and atherectomy. These procedures are primarily directed toward the reduction of stenosis within the vasculature of a patient by either expanding the lumen through the use of a balloon, or ablating or otherwise removing the material making up the stenosis.

While these procedures have shown considerable promise, many patients still require bypass surgery due to such conditions as the presence of extremely diffuse stenotic lesions, the presence of total occlusions and the presence of stenotic lesions in extremely tortuous vessels. Also, some patients are too sick to successfully undergo bypass surgery, and because the above treatments require surgical backup in the case of complications, they are untreatable. Some patients requiring repeat bypass surgeries are also untreatable.

Another method of improving myocardial blood supply is transmyocardial revascularzation (TMR) where channels are formed from the epicardial to the endocardial portions of the heart. TMR relieves ischemia by allowing blood to pass from the ventricle through the channels either directly into other vessels perforated by the channels or into myocardial sinusoids which connect to the myocardial microcirculation. In one method of TMR a $CO_2$ laser is used to produce channels in the ventricle from the epicardium through a portion of the myocardium. This procedure follows a surgical cutdown. External pressure is used to stop bleeding from the ventricle to the outside. The channel is sealed at the epicardial layer. However, the channel's patency in the endocardial and myocardial layers remains questionable. Lasers are an expensive energy source and may be problematic in producing acceptable volumetric tissue ablation rates. RF energy has also been disclosed as an energy source for TMR. A high frequency voltage delivered from an RF electrode is applied to ablate or disintegrate tissue at the heart wall. The RF electrode is axially translated towards the ventricular wall to form a revascularizing channel or artificial vessel from the ventricle to the myocardium in order to increase blood flow. RF electrodes can create very high temperatures which can create an undesired depth of cell necrosis.

A need exists for a cost effective method to increase blood flow to a patient's heart. Another need exists for a method using a cost effective energy source to create revascularzation channels and/or stimulate angiogenesis. Yet another need exists for a method using an ultrasound energy device to improve blood flow to a patient's heart.

SUMMARY OF THE INVENTION

Accordingly, an object of the invention is to provide an apparatus used to improve blood flow to a patient's heart.

Another object of the invention is to provide an apparatus to create revascularzation channels in a patient's heart.

Yet another object of the invention is to provide an apparatus to stimulate angiogenesis in a patient's heart.

A further object of the invention is to provide an energy source which in combination with a medicament stimulates angiogenesis in a patient's heart.

Still another object of the invention is to provide an intravascular catheter with an ultrasound transducer that is useful for creating revascularzation channels and/or stimulating angiogenesis in a patient's heart.

These and other objects of the invention are achieved in a catheter that has an elongated catheter body with a proximal end and a distal end. The elongated catheter body defines a catheter lumen. The elongated catheter body has an introducer distal portion with a tissue piercing distal end. An ultrasound transducer is positioned in the introducer distal portion.

In another embodiment, a tissue piercing member is coupled to an elongated catheter body and is laterally extendable from the distal portion of the elongated catheter body. The tissue piercing member has a tissue piercing distal end. An ultrasound transducer is coupled to the tissue piercing member.

In yet another embodiment, a catheter system includes a guiding catheter and a delivery catheter. The guiding catheter has an elongated guiding catheter body with a guiding catheter lumen. The delivery catheter has an introducer distal portion with a tissue piercing distal end. An ultrasound transducer is coupled to the introducer distal portion.

BRIEF DESCRIPTION OF THE FIGURES

FIG. 1A is a perspective view of a steerable catheter constructed in accordance with the principles of the present invention.

FIG. 1B is a perspective view of a distal portion of the catheter of FIG. 1A.

FIG. 2A is a side cross-sectional view of the distal portion of the catheter of FIG. 1A.

FIGS. 2B and 2C are transverse cross-sectional views taken along lines 2B—2B and 2C—2C, respectively, through the distal portion of the catheter of FIG. 2A.

FIG. 4A is a side cross-sectional view of the handpiece of the catheter of FIG. 1A.

FIG. 4B is a transverse cross-sectional view through line 4B—4B in the handpiece of FIG. 4A.

FIG. 7 is a perspective view of the catheter illustrated in FIG. 1A positioned in a guiding catheter.

DETAILED DESCRIPTION

Figure 3B:
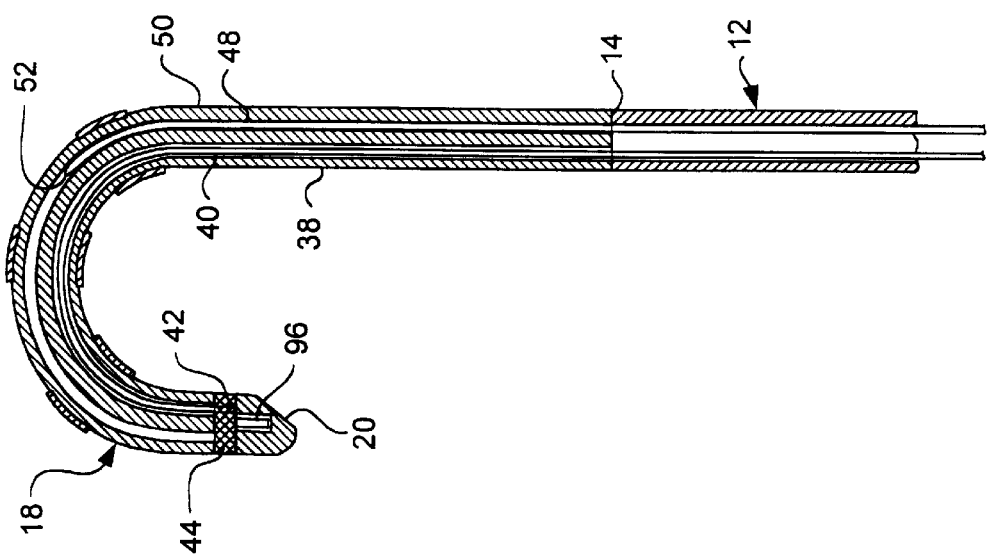
FIGS. 3A and 3B are side cross-sectional views of a distal portion of the catheter of FIG. 1A illustrating two possible tip configurations.

Referring now to FIGS. 1A and 1B, a delivery catheter 10 includes a shaft 12 with a distal portion 14 and a proximal portion 16. An introducer section 18 can be included and fixed to distal portion 14. Introducer section 18 can be deflectable and has a distal end 20 which may be tissue piercing depending on the intended use of delivery catheter 10. When delivery catheter 10 is used for introduction into the heart or other body structure distal end 20 is sufficiently tapered, sharpened and the like to be tissue piercing. In other applications where introducer section 18 is not intended to be introduced into tissue, distal end 20 is not tissue piercing.

A handpiece 22 is secured to proximal portion 16 of shaft 12. Handpiece 22 can include an introducer deflection slide 24, a core wire torque ring 26 and a curvature adjustment slide 28. As illustrated in FIG. 1B, introducer section 18 may be deflected from a straight configuration into a variety of shapes and curvatures, up to at least 270 degree(s) relative to shaft 12, by adjustment of deflection slide 24, curvature adjustment slide 28 and core wire torque ring 26.

Referring now to FIGS. 2A through 2C, shaft 12 has an axial lumen 30 which can receive a guidewire (not shown). In one embodiment, the construction of shaft 12 includes a polyinide or ULTEM(tm) inner tube 32 surrounded by an extruded topcoat 34 of a flexible polymer such as PEBAX. The use of a relatively stiff inner tube 32 within topcoat 34 provides a significant ability to transmit torque along shaft 12. To add additional torsional and bending stiffness to shaft 12, a braided reinforcement 36, usually stainless steel, is embedded in topcoat 34. With this construction, topcoat 34 has a Durometer reading preferably in the range of 35D to 75D. Introducer section 18 can be a unitary extrusion of a flexible polymer that transmits ultrasonic energy, such as PEBAX with a Durometer reading in the range of 30D to 55D. Introducer section 18 may include internal reinforcement using materials such as polyimide or ULTEM. In one embodiment, introducer section 18 can have three axial lumens extending from its proximal end to its distal end, all in communication with axial lumen 30 in shaft 12. All lumens of catheter 10 can be used to introduce various media to the heart, a vessel or other tissue site. Suitable media include but are not limited to drugs, medication, microbubbles, microspheres, an angiogenic stimulation agent, gene therapy and other compositions which provide a therapeutic effect. A first axial lumen 38 is radially offset from the central longitudinal axis of introducer section 18 through which a manipulator wire 40 is disposed. Manipulator wire 40 is coupled at its distal end 42 to an anchor plate 44 at the distal end 30 of introducer portion 18. Preferably, manipulator wire 40 has a diameter of about 0.15 mm and distal end 42 of manipulator wire 40 comprises a ball or similar structure for retaining distal end 42 against anchor plate 44. In a preferred embodiment, axial lumen 38 is radially offset from the central axis of introducer section 18 by an amount equal to approximately 40% to 95% of the radius of introducer section 18. In an exemplary embodiment, introducer section 18 and shaft 12 have a diameter in the range of 5 French (1.65 mm/0.065") to 7 French (2.34 mm/0.092"), with axial lumen 38 being offset in the range of 0.66 mm (0.026") to 2.21 mm (0.087") from the central axis. In one embodiment, a core wire 46 comprises a stainless steel wire with a diameter which ranges from about 0.30–0.64 mm (0.012–0.025"), and preferably about 0.46 mm (0.018"), at its proximal end to about 0.008–0.38 mm (0.007–0.015"), and preferably about 0.20 mm (0.008"), at its distal end for introducer section 18 with diameter of 2.34 mm (0.092").

Introducer portion 18 includes a second axial lumen 48 in which a stiffener wire 50 is slidably disposed. In a preferred embodiment, stiffener wire 50, when advanced into introducer portion 18, will give introducer portion 18 and wire 50 a combined bending stiffness greater than that of introducer section 18 alone, but less than the bending stiffness of shaft 12. In a preferred embodiment, stiffener wire 50 is TEFLON (r) -coated stainless steel and has a diameter over most of its length of about 0.30–0.51 mm (0.012–0.020"), and preferably about 0.46 mm (0.018"), tapers down over a length of about 25 mm (1.0") to a diameter of about 0.08–0.25 mm (0.003–0.010"), and preferably about 0.13 mm (0.005"), for the last 13 mm (0.5") of length. The tip of stiffener wire 50 also preferably has a ball, of a 0.38 mm (0.015") maximum diameter, welded thereto; the use of the ball helps to prevent accidental puncture of lumen 48.

Figure 3A:
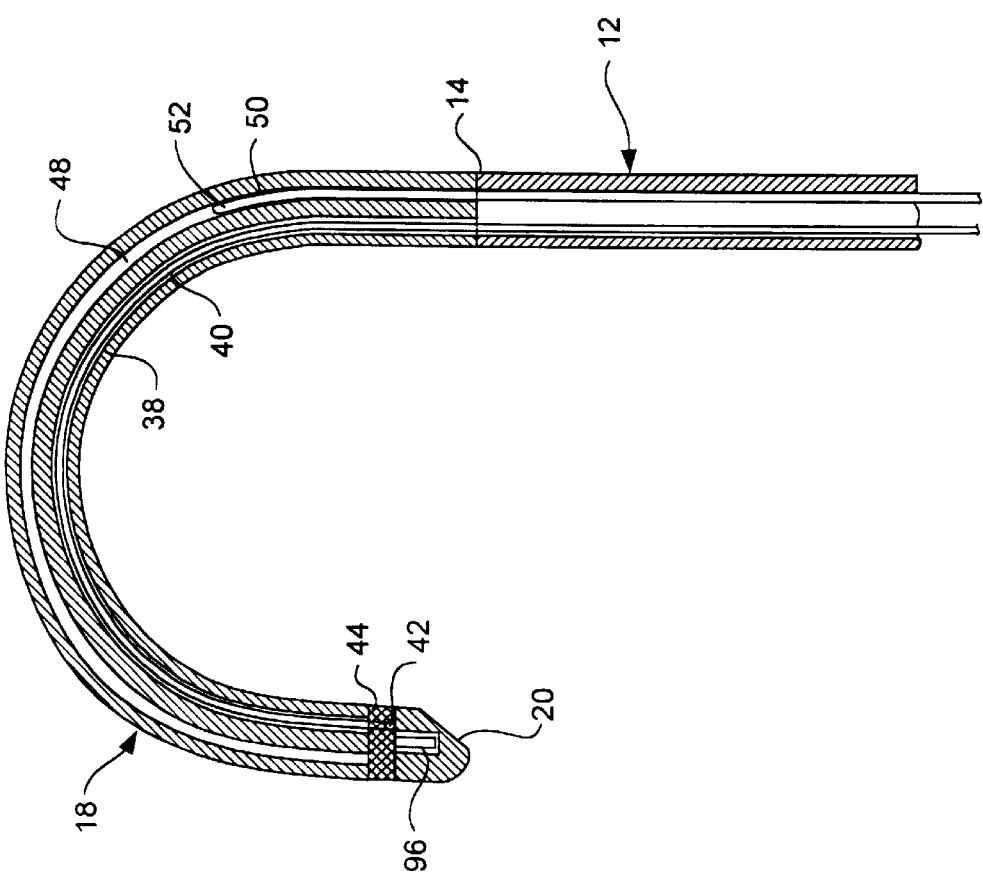

As illustrated in FIGS. 3A and 3B, the curvature imparted to introducer portion 18 may be selectively adjusted by axially translating stiffener wire 50 within lumen 48, while exerting tension on manipulator wire 40. In the example of FIG. 3A, stiffener wire 50 has been positioned such that its distal end 52 extends into a proximal portion of lumen 48 in introducer portion 18. The proximal portion of the deflectable tip in which the stiffener wire is disposed therefore has a bending stiffness which is greater than the remaining distal portion of the deflectable tip. By exerting tension on manipulator wire 40, introducer portion 18 is deflected into a curvature dependent upon the longitudinal position of stiffener wire 50 and the degree of tension applied to the manipulator wire. In FIG. 3B, stiffener wire 50 has been extended distally so that the distal end 52 is closer to the distal end 20 of introducer section 18. The proximal portion of axial lumen 48 occupied by the stiffener wire is now larger than in the example of FIG. 3A, giving the distal portion of introducer section 18 a smaller radius of curvature for a given degree of tension on manipulator wire 40. In this way, when catheter 10 is positioned in the heart, the configuration of the introducer section 18 can be selectively adjusted to impart the desired curvature and shape to introducer portion 18 as appropriate for the size and location of the selected tissue site.

Referring again to FIGS. 2A through 2C, introducer section 18 further includes a third axial lumen 54 through which core wire 46 along with thermocouple wires 56 (coupled to one or more thermal sensors) extend. Thermocouple wires 56, typically copper and constantane, extend introducer section 18 where they are anchored with high temperature adhesive. (As an alternative to stiffener wire 50, an axially extendable tubular stiffener surrounding core wire 46 could be used.) Core wire 46 extends distally through axial lumen 54 and, in one embodiment, is fixed at its distal end to anchor plate 44. Catheters utilizing such a core wire construction are disclosed in U.S. Pat. No. 5,318,525, the complete disclosure of which has been incorporated herein by reference.

Referring now to FIGS. 4A and 4B, handpiece 22 will be described in greater detail. Handpiece 22 includes a housing 58, usually cylindrical in shape, constructed of a rigid material such as ABS, nylon, polycarbonate or polystyrene. Shaft 12 is fixed to housing 58 by means of a mechanical grip or an adhesive and incorporating a strain relief 60. Thermocouple wire 56 extends from shaft 12 through the interior of housing 58. Deflection adjustment slide 24 and curvature adjustment slide 28 have similar construction. An advancement and retraction slide is coupled to a puncturing element, as described below with reference to FIG. 6. Slides 24, 28 include an outer ring 62 disposed about the periphery of housing 58 so as to slide axially thereon. Slots 64 extend axially along housing 58 and are in communication with the interior of the housing. Slide backing plates 66 are disposed in the interior of housing 58 and, in this embodiment, longer than slots 64. Rings 62 are fixed to slide backing plates 66 by means of screws 68, whereby friction between backing plates 66 and the interior of housing 58 may be increased by tightening screws 68. With respect to deflection adjustment slide 24, a hypotube 70 is secured to slide backing plate 66, and manipulation wire 40 extends through hypotube 70. Wire 40 and hypotube 70 are joined such a by crimping, or using an adhesive. A screw 72 in backing plate 66 is tightened to frictionally retain hypotube 70. In the case of curvature adjustment slide 28, stiffener wire 50 extends directly through a bore 74 in slide backing plate 66 and is retained therein by a set screw 76. It may be seen that by sliding deflection adjustment slide 24 and curvature adjustment slide 28 axially along slots 64, the deflection of introducer portion 18 may be appropriately adjusted. The deflected shape of the tip may be retained by appropriate tightening of screws 68 so that backing plates 66 frictionally engage the interior of housing 58. Sliders 24 and 28 act to cover slots 64 to prevent fluid ingress. If desired, flexible external bellows or low Durometer wipers can be used to cover slots 64 allowing the use of shorter sliders 24 and 28. Instead of sliders 24 and 28, other types of drivers, such as rack and pinion or worm gear drivers, could be used.

Core wire torque ring 26 is rotatably coupled to housing 58. Torque ring 26 defines an annular aperture 78 in which is disposed a friction ring 80 of rubber or other high friction material secured to the Torque ring. A limiter ring 82 is fixed to the periphery of housing 58 and defines an annular channel 84. A pin 86 is fixed in a radial position in annular channel 84 and is configured to engage a pin 88 fixed to Torque ring 26 extending radially inward within annular channel 84. Engagement of pins 86, 88 with each other thereby limits the rotational motion of torque ring 26.

Housing 58 includes a partially cylindrical portion 90, see FIG. 4B, for supporting an inner roller 92. Core wire 46 is fixed to inner roller 92 by means of a set screw 94. Inner roller 92 preferably has a knurled outer surface to fictionally engage friction ring 80 bonded to Torque ring 26. In this way, rotation of torque ring 26 rotates inner roller 92, thereby exerting torque on the proximal end of core wire 46. If desired, and with appropriate structural modifications, the functions of slider 24 and ring 26 could be combined into a single control. Preferably, torque ring 26 comprises a ring gear having drive teeth for engaging gear teeth (not shown) on the outer surface of inner roller 92.

Figure 5A:
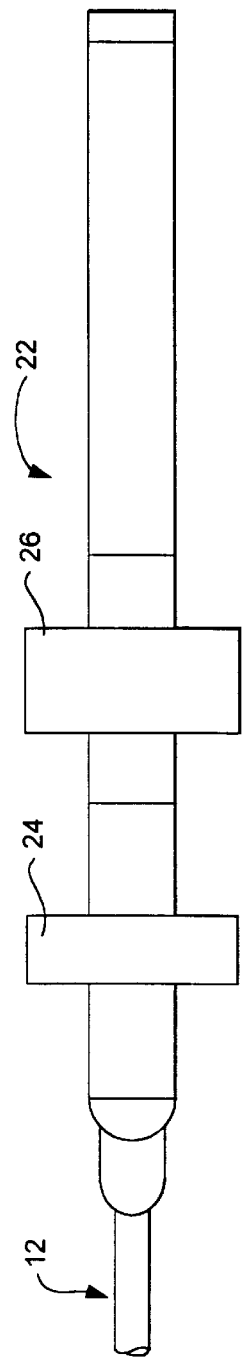
FIGS. 5A—5C are schematics of the handle of the catheter of FIG. 1A, illustrating various configurations of the detachable handpiece sections.
Figure 5B:
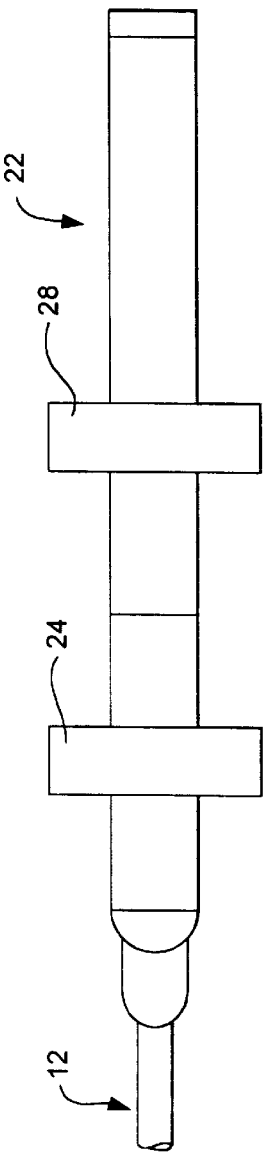
Figure 5C:
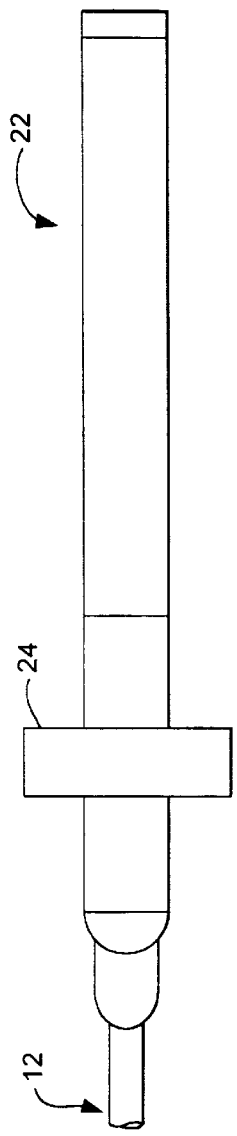

Handpiece 22 can have a modular construction facilitating easy interchange of actuator components, depending upon the capabilities desired in catheter 10. As illustrated schematically in FIGS. 5A through 5C, handpiece 22 has two detachable sections, each section having a universal fitting for attachment to one of the other sections. Each detachable section includes at least one of the actuators for steering and deflecting the introducer portion 18, e.g., deflection slide 24, torque ring 26 or curvature adjustment slide 28. In this way, handpiece 22 may be assembled to include only the components desired by a particular user, thereby minimizing the size, cost and complexity of the device.

Where deflection, rotation and curvature control are all desired in catheter 10, detachable segments having the introducer deflection slide 24, torque ring 26 and curvature adjustment slide 28 can be interconnected by means of snap fittings, as shown in FIGS. 1 and 5A.

Figure 6:
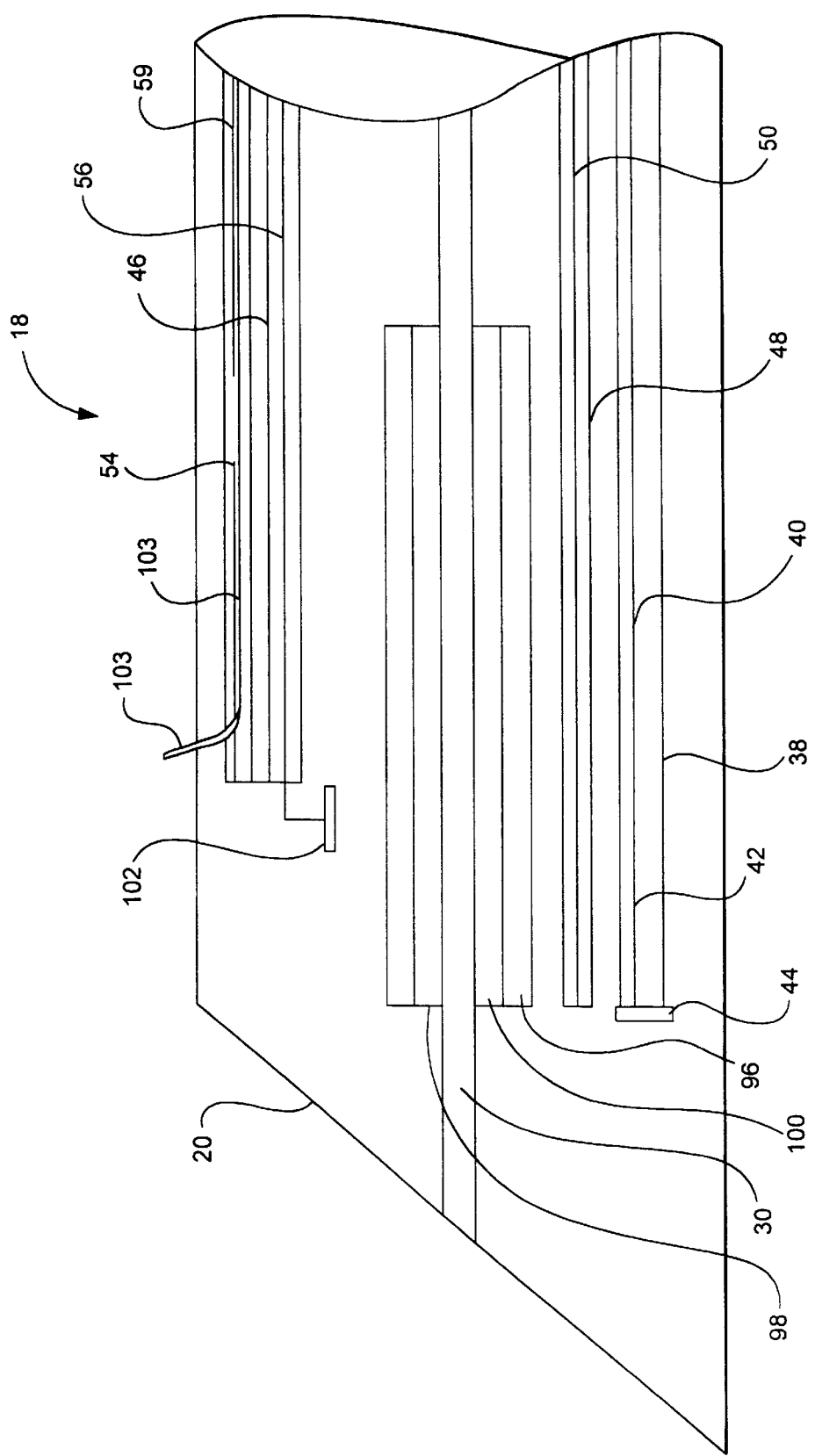
FIG. 6 is a cross-sectional view of the introducer portion of the catheter including the ultrasound transducer.

Referring now to FIG. 6, one or more ultrasound transducers 96 is positioned in introducer section 18. In another embodiment, ultrasound transducers can also be positioned at an exterior of catheter 10. Ultrasound transducer 96 is coupled to an external ultrasound energy source (not shown) and can be positioned around axial lumen 30. Ultrasound transducer can have a variety of different geometric configurations and be made of a variety of different piezoceramics.

Ultrasound transducer 96 can be supported at lumen 30 with one or more supports 98 that create an air or other gaseous chamber 100 between ultrasound transducer 96 and lumen 30. Chamber 100 is filled with a medium which absorbs ultrasound energy or which reduces transmission of ultrasound energy. While it is preferred to use a gaseous media, fluids and solids may also be used. Suitable gaseous media for filling chamber 100 include, but are not limited to, air, nitrogen and the like. Additionally, chamber 100 can be substantially at vacuum. Chamber 100 can have a height from 0.25–10 $\mu$m, more preferably from 0.50–5 $\mu$m and most preferably from 0.0–1.5 $\mu$m.

A thermal sensor 102 is positioned in introducer section 18 and coupled to a thermocouple wire. Suitable frequencies for the ultrasound energy delivered by the ultrasound transducer 18 include, but are not limited to, 20 KHz to 2 MHz. In one embodiment, a puncturing element 103 is contained within introducer portion 18 of catheter 10 and is extendable into the heart, a vessel wall and the like. Puncturing element 103 is positioned in one of axial lumen 30 or lumens 38, 48 or 54. Puncturing element 103 is coupled to advancement and retraction slide 59. A medicament, including but not limited to an angiogenesis stimulation agent, is injected through a lumen of puncturing element 103. Ultrasound transducer 96 is positioned such that it irradiates the injected medicament. This addition of ultrasound energy further mixes, delivers and/or can activate the medicament. In a preferred aspect of the method of the invention, catheter 10 is transluminally positioned through a blood vessel so that introducer portion 18 is within the heart. An axial force is then applied to manipulator wire 40 by sliding introducer deflection slide 24 proximally so as to laterally deflect introducer portion 18 in a first curvature. To further adjust the curvature of introducer section 18 to an optimum configuration, stiffener wire 50 is translated axially relative to the deflectable tip by sliding curvature adjustment slide 28 distally.

In one embodiment, introducer section 18 pierces the heart before energy is delivered. Sufficient energy is delivered to create channels and stimulate angiogenesis with a combination of energy and angiogenesis stimulation agent. In another embodiment, distal end 20 is non-piercing and ultrasound transducer 96 begins to create the revascularzation channels as it is introduced through heart tissue. With regard to FIGS. 1 through 7, catheter 10 is directed through the vasculature into the left ventricle without the use of a guiding catheter. As shown in FIG. 7, catheter 10 can be introduced through a guiding catheter 104 to the selected site, including but not limited to the left ventricle, or other diseased site. Guiding catheters are well known and may be used with catheter 10. A number of channels can be formed from ultrasound transducer 96 from the inner wall, or endocardium, and extend a desired distance through the myocardium without perforating the epicardium. Catheter 10 is inserted into the vasculature of a patient, generally through one of the major vessels, thereby affording access to an area such as a ventricle having an area in need of increased blood circulation due to cardiovascular disease.

Another method of guiding ultrasound transducer 96 into a proper position within the heart is to place the catheter 10 within a deflectable guiding catheter (not shown) having x-y steerability, for an added degree of steerability and control. The positioning of the introducer section 18 may be viewed by esophageal ultrasound imaging or fluoroscope imaging. It may also be desirable to add one or more radiopaque marker bands to catheter 10 for fluoroscopic imaging.

An angiogenesis stimulation agent can be introduced to a selected heart tissue site through catheter 10. Suitable angiogenesis stimulation agents include recombinant proteins, specific inhibitors of protein-protein interactions, tyrosine kinase inhibitors, gene transfer agents and the like. More specifically, the angiogenesis stimulation agent can be a basic fibroblast growth factor (bFGF) or a vascular endothelial growth factor (VEGF).

The FGF growth factor family includes eight structurally-related polypeptides: basic FGF, acidic FGF, int 2, hst 1/k-FGF, FGF-5, FGF-6, keratinocyte growth factor, AIGF (FGF-8) and a glia-activating factor, heparin-binding growth factor purified from the culture supernatant of a human glioma cell line, (Miyamoto, M. et al., Mol. and Cell. Biol., 13(7):4251–4259 (1993). The genes for each are cloned and sequenced. FGF-1 and FGF-2 are characterized as acidic and basic fibroblast growth factors.

EXAMPLE 1

Bacterial Expression and Purification of FGF-13 Protein

The DNA sequence encoding FGF-13 ATCC #97148, is initially amplified using PCR oligonucleotide primers corresponding to the 5' sequences of the processed protein (minus the signal peptide sequence) and the vector sequences 3' to the gene. Additional nucleotides corresponding to the gene are added to the 5' and 3'sequences respectively. The 5' oligonucleotide primer 5' GCCAGACCATG-GAGAATCACCCGTCTCCTAAT 3' (SEQ ID NO:3) contains a Nco restriction enzyme site. The 3' sequence 5' GATTTAAGATCTCGTGAGGGGCTGGGGCCG3' (SEQ ID NO:4) contains complementary sequences to a Bg1II site and is followed by 18 nucleotides of FGF-13 coding sequence.

The restriction enzyme sites correspond to the restriction enzyme sites on the bacterial expression vector pQE-60 (Qiagen, Inc. Chatsworth, Calif.91311). pQE-60 encodes antibiotic resistance (Arnpr), a bacterial origin of replication (ori), an IPTG-regulatable promoter operator (P/O), a ribosome binding site (RBS), a 6-His tag and restriction enzyme sites. pQE-60 was then digested with NcoI and Bg1II. The amplified sequences are ligated into pQE-60 and are inserted in frame with the sequence encoding for the histidine tag and the ribosome binding site (RBS). The ligation mixture is then used to transform E. coli strain M15/rep 4 (Qiagen, Inc.) by the procedure described in Sambrook, J. et al., Molecular Cloning: A Laboratory manual, Cold Spring Laboratory Press, (1989). M15/rep4 contains multiple copies of the plasmid pREP4, which expresses the lacI repressor and also confers kanamycin resistance (KaW). Transformants are identified by their ability to grow on LB plates and ampicillin/kanamycin resistant colonies were selected. Plasmid DNA is isolated and confirmed by restriction analysis. Clones containing the desired constructs are grown overnight(O/N) in liquid culture in LB media supplemented with both Amp (100 ug/ml)and Kan (25 ug/ml). The O/N culture is used to inoculate a large culture at a ratio of 1:100 to 1:250. The cells are grown to an optical density 600(0. D. sup 600) of between 0.4 and 0.6. IPTG ("Isopropyl-B-D-thiogalactopyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chapotropic agent 6 Molar Guanidine HCl. After clarification, solubilized FGF-13 is purified from this solution by chromatography on a Nickel-Chelate column under conditions that allow for tight binding by proteins containing the 6-His tag (Hochuli, E. et al., J. Chromatography 411:177–184 (1984)). The proteins are eluted from the column in 6 molar guanidine HClpH 5.0 and for the purpose of renaturation adjusted to 3 molar guanidine HCl, 100 mM sodium phosphate, 10 mm olar glutathione (reduced) and 2 mm olar glutathione (oxidized). After incubation in this solution for 12 hours the proteins are dialyzed to 10 mmolar sodium phosphate.

EXAMPLE 2

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37 degree(s) C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads. The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and Himd III fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells). Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 3

Synthesis of the bFGF Amino Acid Residue

To synthesize a protein having the mammalian bFGF amino acid residue sequence by recombinant DNA, a double-stranded DNA chain which encodes bFGF s synthetically constructed. In addition to the bFGF-encoding sequences, the DNA chain that is synthesized may contain additional sequences, depending upon vector construction considerations. Typically, the DNA chain is synthesized with linkers at its ends to facilitate insertion into restriction sites within a cloning vector. The DNA chain may be constructed so as to encode the bFGF amino acid sequences as a portion of a fusion polypeptide; and if so generally contains terminal sequences that encode amino acid residue sequences that serve as proteolytic processing sites, whereby the bFGF polypeptide may be proteolytically cleaved from the remainder of the fusion polypeptide. The terminal portions of the synthetic DNA chain may also contain appropriate start and stop signals. To assemble a bFGF-encoding DNA chain, oligonucleotide are constructed by conventional methods, such as procedures described in T. Manatis et al., Cold Spring Harbor Laboratory Manual, Cold Spring Harbor, N.Y. (1982) (hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotide overlap, associating with each other through hydrogen binding between complementary base pairs and thereby forming double stranded chains, in most cases with gaps in the strands. Subsequently, the gaps in the strands are filled in and oligonucleotides of each strand are joined end to end with nucleotide triphosphates in the presence of appropriate DNA polymerases and/or with ligases.

As an alternative to construction of a synthetic DNA chain through oligonucleotide synthesis, cDNA corresponding to bFGF may be prepared. AcDNA library or an expression library is produced in a conventional manner by reverse transcription from messenger RNA (MRNA) from a bFGF-producing mammalian cell line. To select clones containing bFGF sequences, hybridization probes (preferably mixed probes to accommodate the degeneracy of the genetic code) corresponding to portions of the bFGF protein are produced and used to identify clones containing such sequences. Screening of the expression library with bFGF antibodies may also be used, alone or in conjunction with hybridization probing, to identify or confirm the presence of bFGF-encoding DNA sequences in DNA library clones.

The double-stranded bFGF-encoding DNA chain is constructed or modified with insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as E.coli, the DNA chain will be inserted 3' of a promoter sequence, aShine-Delgamo sequence (or ribosome binding site) that is within a 5'non-translated portion and an ATG start codon. The ATG start codon is appropriately spaced from the Shine-Delgarno sequence, and the coding sequence is placed in correct reading frame with the ATG start codon. The cloning vector also provides a 3' non-translated region and a translation termination site. For insertion into a eukaryotic cell, such as a yeast cell or a cell line obtained from a higher animal, the bFGF-encoding oligonucleotide sequence is appropriately spaced from a capping site and incorrect reading frame with an ATG start signal. The cloning vector also provides a 3' non-translated region and a translation termination site.

Prokaryotic transformation vectors, such as pBR322, pMB9, ColE1, pCR1, RP4 and lambda-phage, are available for inserting a DNA chain of the length which encodes bFGF with substantial assurance of at least some expression of the encoded polypeptide. Typically, such vectors are constructed or modified to have a unique restriction site(s) appropriately positioned relative to promoter, such as the lac promoter. The DNA chain may be inserted with appropriate linkers into such a restriction site, with substantial assurance of production of bFGF in a prokaryotic cell line transformed with the recombinant vector. To assure proper reading frame, linkers of various lengths may be provided at the ends of the bFGF-encoding sequences. Alternatively, cassettes, which include sequences, such as the 5' region of the lac Z gene (including the operator, promoter, transcription start site, Shine Delgamo sequence and translation initiation signal), the regulatory region from the tryptophane gene (trp operator, promoter, ribosome binding site and translation initiator), and a fusion gene containing these two promoters called the trp-lac (Tac) promoter are available into which the synthetic DNA chain may be conveniently inserted and then the cassette inserted into a cloning vector of choice.

Similarly, eukaryotic transformation vectors, such as the cloned bovine papilloma virus genome, the cloned genomes of the murine retro viruses, and eukaryotic cassettes, such as the pSV-2 gpt system (described by Mulligan and Berg, Nature 277, 108–114, 1979) the Okayama-Berg cloning system (Mol.Cell Biol., 2: 161–170, 1982), the expression cloning vector described by Genetics Institute (Science 228: 810–815, 1985), are available which provide substantial assurance of at least some expression of bFGF in the transfonned eukaryotic cell line. Production of bFGF or a polypeptide of a similar length can be achieved by producing the polypeptide initially as a segment of a gene-encoded fusion polypeptide. In such case, the DNA chain is constructed so that the expressed polypeptide has enzymatic processing sites flanking the bpFGF amino acid residue sequences. A bFGF-encoding DNA chain may be inserted, for example, into the beta-galactosidase gene for insertion into E. coli, in which case, the expressed fusion polypeptide is subsequently cleaved with proteolytic enzymes to release the bFGF from beta-galactosidase peptide sequences.

EXAMPLE 4

Determination of Bovine bFGF

Frozen bovine pituitaries are homogenized with a Waring blender for 5 minutes in 0.15M ammonium sulfate (4 liter/kg tissue). The pH is adjusted to 4.5 with HCl and the homogenate stirred vigorously for 2 hours. After centrifugation (18,000Xg, 30 minutes) the supernatant is retained. 230 g ammonium sulfate per liter of supernatant are added, the pH is adjusted to 6–6.5 with NaOH and the precipitation is allowed to proceed for 15 hours. After centrifugation of the reaction mixture (18,000Xg, 30 min), the supernatant is retained. 300 g ammonium sulfate is added to each liter of the supernatant. The mixture is stirred for two hours. After centrifugation of the reaction mixture (18,000Xg, 30 min) the pellet is retained, and the cumulative pellets from 3 kg starting tissue dissolved in 200 ml distilled water and dialyzed against 20 liters of distilled water overnight. The pH of the dialyzed retentate is then adjusted to 6, and the solution clarified by centrifugation (12,000Xg, 30 min). The dialyzed retentate constitutes a dialyzed extract.

Basic FGF is subsequently isolated from the dialyzed, clarified extract using three successive protocols. Two of the protocols employ conventional ion-exchange and reverse phase HPLC purification steps. The third method uses heparin-Sepharose affinity chromatography in a key purification step as detailed as follows in the order in which they are performed.

(A) CM-Sephadex (C50) Ion-Exchange Chromatography

A 7X9 cm column of carboxymethyl Sephadex (C50) is washed with 1 liter of 50 mM sodium phosphate, 1.5M sodium chloride, pH 6.0 and then equilibrated with 0.M sodium phosphate, pH 6 slashed zero The dialyzed extract from 3 kg bovine pituitaries is loaded onto the column, and the column is washed sequentially with 0.1M sodium phosphate, pH 6.0 containing a) no NaCl, b) 0.2M NaCl and c) 0.65M NaCl, allowing the OD sub 280 to reach a minimum value before initiating each new wash. Fractions of 18 ml are collected at 3 ml/min at 4 degree(s) C. and subjected to radioimmunoassay.

(B) Heparin-Sepharose Chromatography

The 0.65M NaCl eluate from CM-Sephadex chromatography is loaded onto a 3×3 cm column of heparin-Sepharose (Pharmacia) previously equilibrated with 10 mM Tris-HCl, 0.6M NaCl, pH 7.0 at room temperature. The column is then washed sequentially with 10 mM Tris-HCl, pH 7.0 containing a) 0.6M NaCl and b) 1.1M NaCl, allowing the $OD_{280}$ to reach a minimum value with each wash. The basic FGF is then eluted with a linear gradient in 10 mM Tris-HCl, pH 7.0 containing 100 ml 1.1M NaCl and 100 ml 2M NaCl. Fractions of 5 ml are collected at 0.8 ml/min and subjected to radioimmunoassay.

(C) Reverse Phase Liquid Chromatography

The basic FGF from heparin-Sepharose chromatography is pumped onto a Vydac C-4 (0.46×25 cm) reverse phase column using a 0.1% trifluoroacetic acid (TFA)/ acetonitrile solvent system and eluted at 0.6 ml/min. with a 90 min. gradient of 23% to 35% acetonitrile. Fractions of 3 ml are collected at room temperature and subjected to radioimmunoassay.

In the above mentioned Radioimmunoassays (RIA) for basic FGF, antibodies are generated against a synthetic analog of the amino terminal sequence of basic FGF, [Tyr sup 10 ]bFGF(1–10)which is conjugated to bovine serum albumin, and subsequently used to develop the radioimmunoassay for basic FGF, as described in A. Baird et al. Regulatory Peptides 10, 309–317 (1985). Because it is not possible to quantitate unmodified cysteine by amino acid analysis, cysteine residues are modified either by reduction and alkylation with [sup 14 C] iodoacetamide (New England Nuclear) or oxidization with performic acid. The bFGF in 0.1% TFA/acetonitrile is dried in a 1.5 ml polypropylene microfuge tube in a Speed Vac vacuum centrifuge (Savant, Inc.) just prior to modification. The reduction and alkylation of cysteine residues is performed in order to radioactively label cysteine residues, making it possible to determine which fragments of subsequent cleavage reactions contain cysteine residues. The dried bFGF is dissolved in 0.1 ml deoxygenated 0.5M Tris-HCl pH 7.7,10 mM EDTA, 6M guanidine-HCl. Dithiothreitol is added to a final concentration of 5–10 mM, and the reduction is allowed to proceed at 37degree(s) C for 30 min. A 0.5-fold molar excess of [sup 14C]i odoacetamide (24 mCi/nunole) over total sulfhydryl groups is added, and the incubation continued at 37 degree (s) C. for 60 min. in the dark. The alkylation is terminated by addition of a large excess of dithiothreitolover iodoacetamide, and the alkylated bFGF purified by reverse phase-high performance liquid chromatography.

Performic acid oxidation of cysteine converts cysteine to cysteic acid, and the cysteic acid content of the protein is measurable by amino acid analysis. Performic acid is generated by incubating 9 ml distilled formic acid with 1 ml 30% $H_2O_2$ at room temperature in a tightly capped tube for 1 hour. 0.25 ml of this solution is employed to dissolve the dried bFGF (5–15 nmoles), and the oxidation permitted to continue at 0 degree(s) C for 2.5 hours. Four lyophilizations from distilled water are employed to remove reaction by-products.

Basic FGFs (with cysteines modified by each method described above) are proteolytically and chemically digested to obtain fragments for further analysis, including sequence analysis. Prior to any digestion, the bFGF is dried in a polypropylene microfuge tube in a Speed Vac vacuum centrifuge from volatile RP-HPLC solvents.

In order to obtain multiple, overlapping bFGF fragments, three types of proteolytic digestions of bFGFs, with cysteines modified by each method described above, are performed as follows. The dried bFGF (1–5 nmoles) is dissolved in 0.01 ml 0.5M Tris-HCl pH 7.7, 10 mM EDTA, 6M guanidine-HCl and then diluted to 1 ml with 1% $NH_4HCO_3$. Submaxillaris protease or chymotrypsin is added in a 1/50 (w/w) ratio while digestions with Staphylococcus aureus V8 employed a 1:35 (mol:mol) ratio of enzyme to substrate. Submaxillaris protease cleaves at the C-terminus of arginine; Staphylococcus aureus V8 cleaves at the C-terminus of glutamic acid; and chymotrypsin cleaves at the C-terminus of several amino acid residues having bulky aromatic or hydrophobic groups. Incubations are allowed to proceed overnight at 37 degree(s) C.

Digestion with cyanogen bromide, which cleaves proteins at the C-terminus of Met, are performed on bFGFs, with cysteines modified by each method described above, as follows. The dried, alkylated bFGF (5–6 nmoles) is dissolved with 0.05 ml 70% formic acid and reduced in a solution of 2.9MN-methylmercaptoacetamide in 7% formic acid (R. Heighten et al. Methods in Enzymol. (eds. Hirs., C. & Timasheff, S.) 91: Academic Press, N.Y., pp.549–559 (1983)) for 24 hours at 37 degree(s) C. The alkylated, reduced bFGF is purified by RP-HPLC, dried in a Speed Vac vacuum centrifuge and redissolved in 0.1 ml deoxygenated 70% formic acid. A 100-fold excess of cyanogen bromide is added and the incubation continued at room temperature in the dark overnight.

Reverse phase-high performance liquid chromatography purifications of modified bFGFs and their digestion fragments are accomplished using a Brownlee RP-300 reverse phase column (0.46×25 cm) and a 0.1%TFA/acetonitrile or a 0.1% heptafluorobutyric acid (HFBA)/acetonitrile solvent system. PhNCS-(sup 14 C)-carboxyamidomethylcysteine is identified during sequence analysis by liquid scintillation counting of the residues from the sequencer. The identification of cysteic acid in a given cycle is accomplished by comparison of the amino acid composition of the peptide and the remainder of its sequence as determined by Edman degradation. Carboxypeptidase Y is obtained from Pierce and utilized according to the manufacturer's recommendations. Carboxyl terminal analysis via tritium incorporation is accomplished as previously described (H. Matsuo et al. Protein Sequence Determination (ed., Needleman, S. B.) Springer-Verlag, N.Y., pp. 104–113 (1979)).

EXAMPLE 5

Synthesis of a Mammalian bFGF Gene

Synthesis of a bFGF-encoding DNA chain is accomplished by synthesizing oligonucleotides on an Applied B10 Systems automatic synthesizer with overlapping complementary sequences.

The overlapping oligonucleotides are fused to form a double-stranded DNA chain, gaps are filled in with DNA polymerase and with T4 ligase. Immediately 51 of the FGF-encoding sequence in the sense strand is provided an ATG start signal, which results in an extraneous methionine being added to the N-terminus of the expressed polypeptide. Immediately 3' of the bFGF-encoding sequence is a stop signal. At the 5' end is a Eco RI overhang and at the 3' end is a Sal I overhang, whereby the synthetic DNA strand is directly insertable in the Eco RI and Sal I site of the plasmid pUC8, described by Vieira er al. Gene 14: 259–268 (1982). The DNA strand is annealed into the pUC8 plasmid where it is under the control of the betagalactosidase promoter with the ATG start signal and the Shine Delgarno sequence retained in their natural orientation and association with the promoter.

The recombinant vector, designated bFGF, is transformed into the DH-1 strain of E. coli by the calcium chloride procedure, CSH, supra. The transformed E. coli is cultured in L broth, and ampicillan- resistant strains are selected. Because the DNA chain was inserted into the plasmid in an orientation which could be expected to lead to expression of protein product of the DNA chain, the ampicillan-resistant colonies are screened for reactivity with antiserum raised against bFGF extracted from the pituitary. These colonies are screened by the immunological method of Healfman et al., Proc. Natl. Acad. Sci. USA 80: 31–35 (1983), and colonies reacting positively with bFGF antibody are further characterized. The cells separated from their culture media are lysed, and their supernatant obtained. Supernatant from transformed cells is determined by RIA to be reactive with antibody raised against bFGF. 100 ml. of cell supernatant is obtained, and bFGF is purified therefrom using heparin-Sepharose as described above. Approximately 0.01 mg of bFGF, purified to upwards of 98% by weight of total protein, is produced. The biological activity of the synthetic bFGF, which contains the extraneous N-terminal methionine residue, is tested for biological activity by the ability of the synthetic bFGF to stimulate the proliferation of adult bovine aortic arch endothelial cells in culture, as described in J.Cell Biol. 97: 1677–1685 (1983). Briefly, cells (at passage 3–10) are seeded at a density of 2×10 sup 3 cells/dish on plastic tissue culture dishes and exposed to Dulbecco's modified Eagle's medium (DMEM) supplemented with 10% calf serum. Test samples, at a dilution ranging from 10 sup −1 to 10 sup −3, are added on day 0 and day 2 to the dishes. On day 4, triplicate dishes are trypsinized and counted in a Coulter counter. Background levels are ordinarily 10 sup 5 cells/dish, while those exposed to optimal concentrations of the growth factor can contain as much as 5 to 8×10 sup 5 cells. For a potency assay, a log response curve was established. For this purpose, 10 microliter-aliquots of a dilution (ranging from 10 sup −1 to 10 sup −5) of the original solution made in 0.5%BSA/DMEM were added in triplicate.

The biological (mitogenic) activity of synthetic bFGF is substantially identical to natural, purified bFGF from bovine pituitary cells.

The superfluous N-terminal residue is removable by partial chemical digestion with cyanogen bromide or phenyl isothiocyanate followed by treatment with a strong anhydrous acid, such as trifluoroacetic acid.

The foregoing description of a preferred embodiment of the invention has been presented for purposes of illustration and description. It is not intended to be exhaustive or to limit the invention to the precise forms disclosed. Many modifications and variations will be apparent to practitioners skilled in this art. It is intended that the scope of the invention be defined by the following claims and their equivalents.

What is claimed is:

1. A catheter system, comprising:
   a guiding catheter including an elongated guiding catheter body defining a guiding catheter lumen;
   a delivery catheter defining a plurality of lumens the delivery catheter positionable in the guiding catheter lumen, the delivery catheter including,
   an elongated delivery catheter body;
   an introducer distal portion with a tissue piercing distal end;
   an ultrasound transducer coupled to the introducer distal portion;
   a puncturing element disposed in one of the plurality of lumens and having a distal end extendable radially through an opening in a circumference of the elongated delivery catheter body and into tissue, the puncturing element comprising an axial lumen therethrough for the delivery of a medicament;
   a support member supporting the ultrasound transducer and creating a chamber between the ultrasound transducer and an outer wall of an axial lumen of the plurality of lumens, wherein the chamber is filled with an acoustic reduction medium selected from a group comprising air, a gas, and a vacuum.

2. A catheter system, comprising:
   a guiding catheter including an elongated guiding catheter body defining a guiding catheter lumen; and
   a delivery catheter defining a plurality of lumens the delivery catheter positionable in the guiding catheter lumen, the delivery catheter including,
   an elongated delivery catheter body;
   an introducer distal portion with a tissue piercing distal end;
   an ultrasound transducer coupled to the introducer distal portion;
   a puncturing element disposed in one of the plurality of lumens and having a distal end extendable radially through an opening in a circumference of the elongated delivery catheter body and into tissue, the puncturing element comprising an axial lumen therethrough for the delivery of a medicamen;
   a support member supporting the ultrasound transducer and creating a chamber between the ultrasound transducer and an outer wall of an axial lumen of the plurality of lumens, wherein the chamber is filled with an acoustic reduction medium selected from a group comprising air, a gas, and a vacuum; and
   a handpiece at a proximate end, wherein the handpiece includes at least one adjustment control mechanism manipulable for deflecting the introducer distal portion from a straight configuration into a variety of shapes.

3. A catheter system, comprising:
   a guiding catheter including an elongated guiding catheter body defining a guiding catheter lumen; and
   a delivery catheter defining a plurality of lumens, the delivery catheter positionable in the guiding catheter lumen, the delivery catheter including,
   an elongated delivery catheter body;
   an introducer distal portion with a tissue piercing distal end;
   an ultrasound transducer coupled to the introducer distal portion;
   a puncturing element disposed in one of the plurality of lumens and having a distal end extendable radially through an opening in a circumference of the elongated delivery catheter body and into tissue, the puncturing element comprising an axial lumen therethrough for the delivery of a medicamen:
   a support member supporting the ultrasound transducer and creating a chamber between the ultrasound transducer and an outer wall of an axial lumen of the plurality of lumens, wherein the chamber is filled with an acoustic reduction medium selected from a group comprising air, a gas, and a vacuum; and
   a handpiece at a proximate end, wherein the handpiece includes at least one adjustment control mechanism manipulable for deflecting the introducer distal portion from a straight configuration into a variety of shapes, and wherein the at least one adjustment control comprises a deflection slide.

4. A catheter system comprising:
   a guiding catheter including an elongated guiding catheter body defining a guiding catheter lumen; and
   a delivery catheter defining a plurality of lumens, the delivery catheter positionable in the guiding catheter lumen, the delivery catheter including,
   an elongated delivery catheter body;
   an introducer distal portion with a tissue piercing distal end;
   an ultrasound transducer coupled to the introducer distal portion;
   a puncturing element disposed in one of the plurality of lumens and having a distal end extendable radially through an opening in a circumference of the elongated delivery catheter body and into tissue, the puncturing element comprising an axial lumen therethrough for the delivery of a medicamen:
   a support member supporting the ultrasound transducer and creating a chamber between the ultrasound transducer and an outer wall of an axial lumen of the plurality of lumens, wherein the chamber is filled with an acoustic reduction medium selected from a group comprising air, a gas, and a vacuum; and
   a handpiece at a proximate end, wherein the handpiece includes at least one adjustment control mechanism manipulable for deflecting the introducer distal portion from a straight configuration into a variety of shapes, and wherein the at least one adjustment control comprises a curvature adjustment slide.

5. A catheter system comprising:
   a guiding catheter including an elongated guiding catheter body defining a guiding catheter lumen; and
   a delivery catheter defining a plurality of lumens, the delivery catheter positionable in the guiding catheter lumen, the delivery catheter including,
   an elongated delivery catheter body;
   an introducer distal portion with a tissue piercing distal end;
   an ultrasound transducer coupled to the introducer distal portion;
   a puncturing element disposed in one of the plurality of lumens and having a distal end extendable radially through an opening in a circumference of the elongated delivery catheter body and into tissue the puncturing element comprising an axial lumen therethrough for the delivery of a medicamen;
   a support member supporting the ultrasound transducer and creating a chamber between the ultrasound transducer and an outer wall of an axial lumen of the plurality of lumens, wherein the chamber is filled with an acoustic reduction medium selected from a group comprising air, a gas, and a vacuum; and a hand piece at a proximate end wherein the handpiece includes at least one adjustment control mechanism manipulable for deflecting the introducer distal portion from a straight configuration into a variety of shapes, and wherein the at least one adjustment control comprises a core wire torque ring.

* * * * *

SEQUENCE LISTING

<160> NUMBER OF SEQ ID NOS: 14

<210> SEQ ID NO 1
<211> LENGTH: 640
<212> TYPE: DNA
<213> ORGANISM: Homo sapiens

<400> SEQUENCE: 1

```
ccgcctgctg cccaacctca ctctgtgctt acagctgctg attctctgct gtcaaactca      60
gggggagaat cacccgtctc ctaattttaa ccagtacgtg agggaccagg gcgccatgac     120
cgaccagctg agcaggcggc agatccgcga gtaccaactc tacagcagga ccagtggcaa     180
gcacgtgcag gtccccgggc gtcgcatctc cgccaccgcc gaggacggca acaagtttgc     240
caagctcata gtggagacgg acacgtttgg cagccgggtt cgcatcaaag gggctgagag     300
tgagaagtac atctgtatga acaagagggg caagctcatc gggaagccca gcgggaagag     360
```

-continued

```
caaagactgc gtgttcacgg agatcgtgct ggagaacaac tatacggcct tccagaacgc      420
ccggcacgag ggctggttca tggtcttcac gcggcagggg cggccccgcc aggcttcccg      480
cagccgccag aaccagcgcg aggcccactt catcaagcgc tctaccaag gccagctgcc       540 cttccccaac cacgccgaga agcagaagca gttcgagttt gtgggctccg cccccacccg      600
tcggaccaag cgcacacggc ggccccagcc cctcacgtag                            640
```

<210> SEQ ID NO 2
<211> LENGTH: 210
<212> TYPE: PRT
<213> ORGANISM: Homo sapiens

<400> SEQUENCE: 2

```
Arg Leu Leu Pro Asn Leu Thr Leu Cys Leu Gln Leu Ile Leu Cys
1               5                   10                  15

Cys Gln Thr Gln Gly Glu Asn His Pro Ser Pro Asn Phe Asn Gln Tyr
            20                  25                  30

Val Arg Asp Gln Gly Ala Met Thr Asp Gln Leu Ser Arg Arg Gln Ile
        35                  40                  45

Arg Glu Tyr Gln Lys Arg Thr Ser Gly Lys His Val Gln Val Pro Gly
    50                  55                  60

Arg Arg Ile Ser Ala Thr Ala Glu Asp Gly Asn Lys Phe Ala Lys Leu
65                  70                  75                  80

Ile Val Glu Thr Asp Thr Phe Gly Ser Arg Val Arg Ile Lys Gly Ala
                85                  90                  95

Glu Ser Glu Lys Tyr Ile Cys Met Asn Lys Arg Gly Lys Leu Ile Gly
            100                 105                 110

Lys Pro Ser Gly Lys Ser Lys Asp Cys Val Phe Thr Glu Ile Val Leu
        115                 120                 125

Glu Asn Asn Tyr Thr Ala Phe Gln Asn Ala Arg His Glu Gly Trp Phe
    130                 135                 140

Met Val Phe Thr Arg Gln Gly Arg Pro Arg Gln Ala Ser Arg Ser Arg
145                 150                 155                 160

Gln Asn Gln Arg Glu Ala His Phe Ile Lys Arg Leu Tyr Gln Gly Gln
                165                 170                 175

Leu Pro Phe Pro Asn His Ala Glu Lys Gln Lys Gln Phe Glu Phe Val
            180                 185                 190

Gly Ser Ala Pro Thr Arg Arg Thr Lys Arg Thr Arg Pro Gln Pro
        195                 200                 205

Leu Thr
    210
```

<210> SEQ ID NO 3
<211> LENGTH: 32
<212> TYPE: DNA
<213> ORGANISM: Artificial Sequence
<220> FEATURE:
<223> OTHER INFORMATION: PCR primer

<400> SEQUENCE: 3

```
gccagaccat ggagaatcac ccgtctccta at                                    32
```

<210> SEQ ID NO 4
<211> LENGTH: 30
<212> TYPE: DNA
<213> ORGANISM: Artificial Sequence
<220> FEATURE:

-continued

```
<223> OTHER INFORMATION: PCR primer

<400> SEQUENCE: 4
gatttaagat ctcgtgaggg gctggggccg                                       30

<210> SEQ ID NO 5
<211> LENGTH: 30
<212> TYPE: DNA
<213> ORGANISM: Homo sapiens

<400> SEQUENCE: 5
ctagtggatc ccgagaatca cccgtctcct                                       30

<210> SEQ ID NO 6
<211> LENGTH: 30
<212> TYPE: DNA
<213> ORGANISM: Homo sapiens

<400> SEQUENCE: 6
cgacttctag aacctcgggg atctggctcc                                       30

<210> SEQ ID NO 7
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 7

Gly Xaa Leu Xaa Ser Xaa Xaa Xaa Xaa Xaa Xaa Asp Cys Xaa Phe Xaa
1               5                   10                  15

Glu

<210> SEQ ID NO 8
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 8

Gly Xaa Leu Xaa Thr Xaa Xaa Xaa Xaa Xaa Xaa Asp Cys Xaa Phe Xaa
1               5                   10                  15

Glu

<210> SEQ ID NO 9
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 9

Gly Xaa Leu Xaa Ala Xaa Xaa Xaa Xaa Xaa Xaa Asp Cys Xaa Phe Xaa
1               5                   10                  15

Glu

<210> SEQ ID NO 10
<211> LENGTH: 17
<212> TYPE: PRT
<213> ORGANISM: Homo sapiens
```

```
<220> FEATURE:
<221> NAME/KEY: misc_feature
<223> OTHER INFORMATION: X=Undetermined amino acid

<400> SEQUENCE: 10

Gly Xaa Leu Xaa Gly Xaa Xaa Xaa Xaa Xaa Asp Cys Xaa Phe Xaa
1               5                   10                  15

Glu

<210> SEQ ID NO 11
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 11

Gly Xaa Leu Xaa Ser Xaa Xaa Xaa Xaa Xaa Glu Cys Xaa Phe Xaa
1               5                   10                  15

Glu

<210> SEQ ID NO 12
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 12

Gly Xaa Leu Xaa Thr Xaa Xaa Xaa Xaa Xaa Glu Cys Xaa Phe Xaa
1               5                   10                  15

Glu

<210> SEQ ID NO 13
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 13

Gly Xaa Leu Xaa Ala Xaa Xaa Xaa Xaa Xaa Glu Cys Xaa Phe Xaa
1               5                   10                  15

Glu

<210> SEQ ID NO 14
<211> LENGTH: 17
<212> TYPE: PRT
<213> ORGANISM: Homo sapiens
<220> FEATURE:
<221> NAME/KEY: misc_feature
<223> OTHER INFORMATION: X=Undetermined amino acid

<400> SEQUENCE: 14

Gly Xaa Leu Xaa Gly Xaa Xaa Xaa Xaa Xaa Glu Cys Xaa Phe Xaa
1               5                   10                  15

Glu
```